US006227031B1

(12) United States Patent
Krajewski et al.

(10) Patent No.: US 6,227,031 B1
(45) Date of Patent: May 8, 2001

(54) METHOD AND APPARATUS FOR CALIBRATING GAS SAMPLERS

(75) Inventors: Charles A. Krajewski, Bridgeville; Peter M. Hall, McMurray, both of PA (US)

(73) Assignee: SKC, Inc., Eighty Four, PA (US)

( * ) Notice: Subject to any disclaimer, the term of this patent is extended or adjusted under 35 U.S.C. 154(b) by 0 days.

(21) Appl. No.: 09/325,333

(22) Filed: Jun. 3, 1999

(51) Int. Cl.⁷ .................................................. G01N 21/00
(52) U.S. Cl. ................................ 73/1.06; 73/1.16
(58) Field of Search ........................ 73/1.01, 1.06, 73/1.16, 1.34, 863.21, 863.23, 863.03

(56) References Cited

U.S. PATENT DOCUMENTS

| | | | |
|---|---|---|---|
| 3,994,153 | 11/1976 | Gussman et al. | 73/3 |
| 4,246,788 * | 1/1981 | Olin et al. | 73/863.03 |
| 4,269,059 * | 5/1981 | Baker | 73/863.03 |
| 4,375,667 | 3/1983 | Buchan | 364/418 |
| 4,389,903 * | 6/1983 | Bertone et al. | 73/863.03 |
| 4,569,235 | 2/1986 | Conkle et al. | 73/863.03 |
| 5,107,713 | 4/1992 | Peck et al. | 73/863.02 |
| 5,440,925 | 8/1995 | Padden et al. | 73/253 |
| 5,456,107 | 10/1995 | Padden et al. | 73/239 |
| 5,551,311 | 9/1996 | Ogden et al. | 73/863.31 |
| 5,646,357 | 7/1997 | Ogden et al. | 73/863.31 |

* cited by examiner

*Primary Examiner*—Robert Raevis
(74) *Attorney, Agent, or Firm*—William L. Krayer

(57) ABSTRACT

A method for calibrating a personal air sampler. A desired flow rate is set, the actual rate measured and recorded through a plurality of runs, the results are automatically averaged and compared to the desired flow and the pump is automatically adjusted accordingly. The process may be repeated for a plurality of selected flow rates, and a best-fit curve computed to cover the entire range. Stability is tested by a series of sets of runs to determine erratic behavior, and an overall calibration is conducted by performing such a series of runs at each of several set point flows.

16 Claims, 2 Drawing Sheets

METHOD AND APPARATUS FOR CALIBRATING GAS SAMPLERS

TECHNICAL FIELD

This invention relates to small personal air samplers and particularly to their calibration for accurate readings of air or gas flow and sample volume.

BACKGROUND OF THE INVENTION

Prior to the present invention, the calibration of personal air samplers involved in large part empirically obtained readings and sometimes unreliable manipulation by the user. Many of the calibrators employed bubble flowmeters.

An early patent to Gussman et al, U.S. Pat. No. 3,994,153, was directed to the calibration of the rotameter used to measure flow.

Conkle et al, in U.S. Pat. No. 4,569,235, maintain substantially constant air flow in an air sampler by monitoring flow rate change and using a signal representative of the flow rate change to manipulate the pump.

Padden et al, in U.S. Pat. Nos. 5,456,107 and 5,440,925, describe generating electrical signals representing flow rates and as a function of known volumes in one or more enclosures traversed by a piston. It is suggested that these signals may be used in data logging and report generation, but the device is not tied directly to the sampler pump for calibration in the manner of the present applicants.

Flow rates are calculated from the velocity of air in a sampler, as described by Buchan in U.S. Pat. No. 4,375,667. The flow rates are then integrated within the instrument over a sample period to provide an indication of the volume sampled, which the authors say enables them to obviate a calibration step. This disclosure employs a microprocessor and converters for processing the data obtained, but still may be said to calibrate only for a current sample and not as a standard for use over an extended period of time.

Ogden et al, in U.S. Pat. No. 5,551,311, uses a personal computer and describes a calibrating apparatus connected to it from the sampler. The system, however, does not utilize the data in the manner of applicants. See also Ogden et al U.S. Pat. No. 5,646,357.

Peck et al, in U.S. Pat. No. 5,107,713, describes a procedure which is manually repeated for several flow measurement readings; the user is prompted to enter the readings on a CPU, which further manipulates them based on an empirical compilation to establish a relationship between air flow, pulse width modulation, and pump motor RPM, using also a flow calibration meter. As described, the device is essentially self-calibrating, but does not tie the data generation to the calibrating device as applicants do.

The prior art approaches to calibration are not conducive to the calibration of a large number of personal air samplers within a short period of time. One may, for example, manually change the speed of the pump and then read a calibrator such as that described by Ogden et al above, marking down the data as it is collected. This process is susceptible to errors in setting the pump, recording the setting of the pump, and recording the reading of the calibrator. Over a period of time and a series of calibrations, errors are statistically likely.

SUMMARY OF THE INVENTION

Our invention includes a method of calibrating an air sampler at one desired flow rate or several wherein, for each desired flow rate, a plurality of air flow rates are averaged and analyzed, more or less automatically, for accuracy and stability. Where a range of flow rates is calibrated, a best-fit curve and/or a function representing it is generated. In either case—a single point or where a range of flow rates is calibrated—pump action is varied to deliver the desired flow.

Our technique permits the user to calibrate a large number of air samplers within a short period of time while minimizing the possibility of errors in entering data such as may happen with the Peck et al system mentioned above. In addition, our system is readily performed frequently and, perhaps more importantly, minimizes the possibility of introducing human error. Records may be maintained of the data obtained in and used for calibration.

We calibrate the air processing of a personal air sampler by (a) setting a desired air flow rate in the air sampler, (b) generating a signal representing a measured air flow rate through the air sampler set at the desired air flow rate, (c) recording the measured air flow rate in a data recorder (d) repeating steps (b) and (c) through at least one iteration (preferably a total of at least three repetitions), and (d) averaging at least two (preferably at least four) of the recordings so obtained. The average is compared to the setting of the desired air flow rate to determine the degree of difference, which is converted to a signal to be used as feedback for adjustment of voltage or power to the pump, or otherwise to adjust its output. The feedback signal may also be recorded and thereafter used to power the pump at the new level each time the tested air flow rate is desired. The pump and sampler are therefore calibrated for that particular desired air flow rate. Note that the difference of the measured flow from the desired flow, and the average difference from the setting, are both treated as positive numbers whether they are above or below the compared point.

Thus a straightforward calibration of a single desired air flow will result in the power supply to the pump being controlled to energize the pump to the degree necessary to achieve the desired air flow rate. As the typical sampler is battery-powered, the adjustment is preferably made to the voltage supplied to the pump. The new voltage will thereafter be used for that desired air flow rate until the sampler is calibrated again at that point.

But our procedure also guards against the possibility that an average of two or more measurements may be very close to the desired rate, while the individual measurements which make up the average are quite removed from the desired rate. A high total difference from the average indicates instability. Therefore we conduct the test for stability described below. Unlike the results of the averaging test, the results of the stability test are not used to adjust the power input to the pump. They are used to determine whether to discontinue use of the sampler.

To determine stability of the sampler, our procedure continues beyond the above recited sequence of steps with the steps of (e) determining and recording the absolute difference between each of the recordings and the average so obtained, (f) totaling the differences obtained, (g) expressing the total of differences in terms of a percentage of the average, and (h) comparing the percentage to a predetermined acceptable percentage. This percentage value may be used to decide whether to continue or discontinue the sampler in service, or the more extended procedure described further below may be followed.

While we speak throughout of personal air samplers, it should be understood that the same procedures and techniques may be used with respect to gases and gaseous media other than air, where the samplers are used to collect and/or measure contaminants, aerosols, microorganisms, and concentrations of various substances and other gases.

When we speak of "signals", we include not only the usual and typical electrical signals, but also pneumatic or other signals. They may be continuous (analog) or discrete (digital). Note also that the action of the pump may be varied by varying the voltage or power to it, by braking, actuation of a clutch, adjustment of the pump stroke, and/or any other practical means.

DETAILED DESCRIPTION OF THE INVENTION

Figure 1:
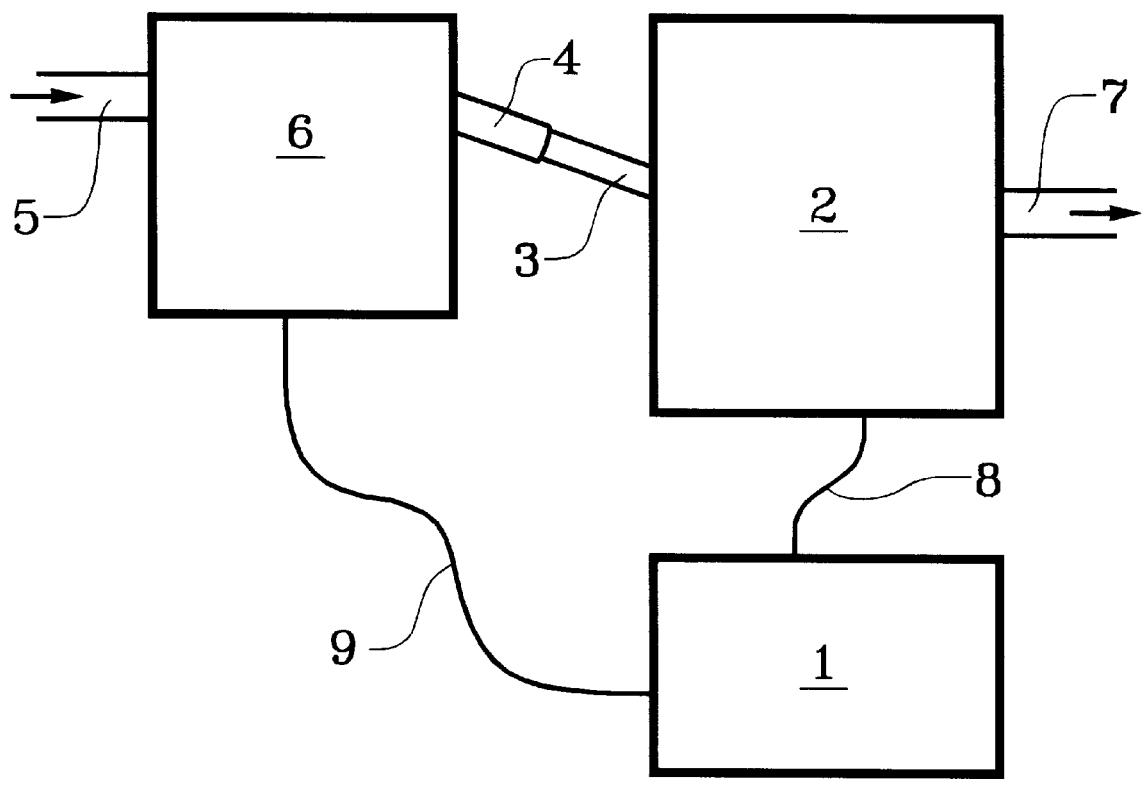
FIG. 1 is a flow sheet of our process.

In a preferred, more elaborate, practice of our invention, we average a series of at least four flow measurements a, b, c, and d through an air sampler set at a desired flow rate and determine the total deviation of the four measurements from the average thereof. If the total deviation is higher than a predetermined maximum, we again measure the flow through the air sampler set at the desired flow rate; the new flow measurement may be designated flow measurement e. We then determine the total deviation of flow measurements b, c, d, and e from the average thereof. If the total deviation of flows b, c, d, and e is higher than a predetermined maximum, we take a new measurement of the flow, f, through the sampler set at the desired flow rate and again determine the total deviation, this time of the individual measured flows c, d, e, and f from the average thereof; if the total deviation of the flows c, d, e, and f is higher than a predetermined maximum, a further flow g is measured through the air sampler set at the desired flow rate and again the total deviation of flow measurements d, e, f, and g is determined from the average thereof. Then, if the total deviation of flows d, e, f, and g is higher than a predetermined maximum, we again measure the flow, h, through the air sampler set at the desired flow rate and determine the total deviation of flow measurements e, f, g, and h from the average thereof, whereby if the total deviation is greater than a desired maximum, the personal air sampler is determined to be unstable. Normally and preferably, the pump remains running throughout the above outlined procedure, but we do not rule out a procedure utilizing discrete pumping action. Note that this describes a series of five overlapping or cascading routines, beginning with measurements a, b, c, d and b, c, d, e. Four such routines are normally sufficient and four is our preferred number, but any number of sequential routines in excess of one may be used.

Persons skilled in the art will realize that the above procedures may be varied and that the underlying principle is to take at least two flow readings at the same setting, average the readings, and determine the difference of those readings from their average, for a comparison with a predetermined standard of overall difference. Thus the test for that particular setting may be satisfactory if the readings are generally near the target flow rate, either over or below. If the difference between the average of the measured flow rates and the desired flow rate is greater than the predetermined standard of overall difference, an electrical signal is generated to adjust the pump in a manner to bring the air flow rate into acceptability. But even if the average is very close to the target flow rate, our test for stability may demonstrate that there are large differences above and below the target flow, meaning that performance is erratic and imprecise. We also recognize that it may take a certain period of time for the sampler to stabilize to the conditions of the test, and accordingly we pass it through several sequential and, preferably, overlapping tests. Hence, in the above description, we average the first, second, third and fourth result, then the second, third, fourth and fifth result, then the third, fourth, fifth and sixth result, and so forth to at least the fifth, sixth, seventh and eighth runs. This sequence can be followed in any case, but is preferred if the first result is unsatisfactory. In a preferred version of our procedure, we discard the results of the first run regardless of whether it is satisfactory, and proceed to a series of at least two (or other desired number higher than two, preferably four) runs.

After the above described process is employed for a particular selected (desired) flow rate, a different flow rate may be selected and the process repeated for the new flow rate. The above described procedures can be performed automatically by programming the pump and microprocessor to perform the various steps. Thus, although a large number of steps and samples can be processed, particularly when a quantity of personal samplers is to be tested, the procedure can be accomplished conveniently and in good time.

Our invention includes the programming of a microcomputer or controller to perform automatically both the individual selected flow calibration and calibration over a range of flow rates followed by generation of a best-fit curve using well-known algorithms.

FIG. 1 is a flow sheet of our invention. Controller 1 performs several functions which may be separated into several different pieces of equipment or combined into one, or may be built into the air sampler 2 or the calibrator 6. It is programmed to carry out the tests and calibrations in the sequences described herein, on command of the operator, who initiates the process. Air sampler 2 includes an air pump which draws air through intake 3, passes it through its sampling system, and then through air discharge 7. Air intake 3 is normally open to the air, but we connect it through duct 4 to calibrator 6, which includes a flow transducer. Calibrator 6 takes in air through air intake 5 and measures the air flow to and through it as it passes through from air intake 5 to exit duct 4. The flow transducer in calibrator 6 generates an electrical signal representative of the measured flow and transmits it over electrical connection 9 to controller 1, which includes a data recorder and microcomputer. The air flow is recorded by the data recorder. After a preferably adjustable preset interval, a second air flow is measured and recorded in the same manner. The microcomputer may then average the recorded values or wait for additional recordings, depending on the programmed sequence. The intervals between the measurements, the programmed sequence of the procedure, and all other controls and data collection of the system are communicated either through connection 8 between the controller 1 and sampler 2 or connection 9 between controller 1 and calibrator 6. The calibrator 6 is in this instance located on the intake of the sampler 2 at least partly because the operation of sampler 2 calls for discharge to atmosphere. For other types of samplers and/or sampler pumps, the calibrator may effectively measure flow from the discharge. Any of the values measured, generated or recorded may be displayed for the operator, preferably on the sampler if the controller 1 is built into the sampler 2.

Following is a description of a Single Point Calibration Process program in pseudo-code, where k is the flow reading count and F is the volumetric flow measurement from a Bios DRYCAL calibrator:

1 k=0
2 k=k+1
3 if(k>8) Error "Too much variation among readings". END
4 F=Reading from DRYCAL
5 Avg[k]=flow
6 If(k<4) goto 2
7 $F_{avg}$=(Avg[k]+Avg[k-1]+Avg[k-2]+Avg[k-3])/4
8 Calculate the variation between $F_{avg}$ and Avg[k] . . . Avg[k-3]
9 If(variation>acceptable limit) goto 2
10 If(|FlowDesired-$F_{avg}$|<10 ml/min) goto 13
11 Adjust voltage in pump to make run faster or slower as indicated
12 Goto 1
13 Successful single point calibration The numbers 8 and 4 in lines 3 and 6 are typical but not essential and may be varied considerably, as explained elsewhere herein.

Following is a Full Calibration Process program in pseudo-code where k and F are as above and E is the voltage that the sampler provides internally to control motor speed for the pump mechanism (i.e. more volts=higher flow), x[i] is the flow rate of the i'th measurement and y[i] is the voltage for the i'th measurement:

1 E=initial value (a minimum voltage that makes the pump operate very slowly or not at all)
2 k=0
3 k=k+1
4 if(k>8) Error "Too much variation among readings". END
5 F=Reading from DRYCAL
6 Avg[k]=F
7 If(k<4) goto 3
8 $F_{avg}$=(Avg[k]+Avg[k-1]+Avg[k-2]+Avg[k-3])/4
9 Calculate the variation between $F_{avg}$ and Avg[k]. . . Avg[k-3]
10 If(variation>acceptable limit) goto 3
11 x[i]=$F_{avg}$
12 y[i]=E
13 if (F>3000 ml/min) goto 17
14 E=E+ΔE (raise the voltage by a small amount)
15 If (E=max voltage) Error "Cannot achieve 3000 mL/min". END
16 Goto 2
17 // Final Calculations
18 Find last i where x[i]<750. Call it x[first]
19 Use last i (if no errors occurred x[i] will be >3000) Call it x[last]
20 Calculate a best-fit curve from (x[first], y[first]) to (x[last], y[last]).
21 When done, we will have a curve y=f(x)
22 We can then plug our desired flow (x) into the equation. It will calculate 'y', the voltage that we need to most accurately achieve that flow.

Note that the program literally does not input desired or selected flow rates, but rather simply incrementally increases the voltage and measures the resulting flow rate, to generate the curve. After full calibration, the sampler is in effect a secondary standard at any flow rate selected in its range.

EXAMPLE 1

An SKC AIRCHEK 2000 air sampler (obtained from SKC, Inc., Eighty Four PA and constructed as described in U.S. Pat. No. 5,892,160), was to be calibrated according to our technique. It was accordingly set to a desired flow rate of 1000 milliliters per minute and connected to a DRYCAL DC-Lite calibrator model 717-01, obtained from BIOS, Inc., Pompton Plains, N.J., using our interfacing controller, a CALCHEK communicator (source—SKC, Inc., Eighty Four PA), which takes the output from the calibrator to the pump. The process was initiated by turning the system on, permitting the pump to activate and initiating the single point controlled procedure described above. The DRYCAL calibrator includes a flowmeter or flow transducer; it is itself calibrated and may be considered a primary standard. It reads the actual flow and converts the flow to an electrical signal representative of the flow. The flow may be converted to either a digital or analog signal, or both. A representative series of data, which can displayed or printed, is shown in Table 1:

TABLE 1

| Desired Flow Setting - 1000 mL/min | | | |
| --- | --- | --- | --- |
| Flow | Reading | | Difference from Average |
| 1 | discarded | | — |
| 2 | 994 | | 10 |
| 3 | 1009 | | 5 |
| 4 | 1002 | | 2 |
| 5 | 1011 | | 7 |
| Average | 1004 | Sum | 24 |

An immediate observation is that the average flow was above the desired flow rate of 1000 mL/min. Although the sampler's performance is acceptable at the setting of 1000 mL/min., the difference of 4 mL/min. from the average may be used as automatic feedback to adjust the voltage delivered to the pump for the desired flow setting. After the same type of data collection is made at several selected flow rates, the microcomputer may generate a best-fit curve y=f(x) where y is the voltage to be applied and x is the flow set point. This information is used thereafter for any desired flow rate in the entire range of the sampler. Thus our system can be used to control the pump, or to calibrate the air sampler, over a range of air flow rates.

For the data in Table 1, the limit for the total difference for the four points had been set at 6% of the average, considerably above the variation here, which is slightly less than 2.4% of the average, and accordingly the sampler successfully passed the stability test at the input flow rate of 1000 mL/min.

Although, as noted above, the BIOS calibrator is taken as the primary standard, it is subject to possible error as well as the sampler. A plurality of measurements is used to obtain at least a minimum sampling base. These are averaged for comparison to the selected flow, in order to minimize the effect of possible errors originating in either the sampler or the calibrator or both.

Figure 2:
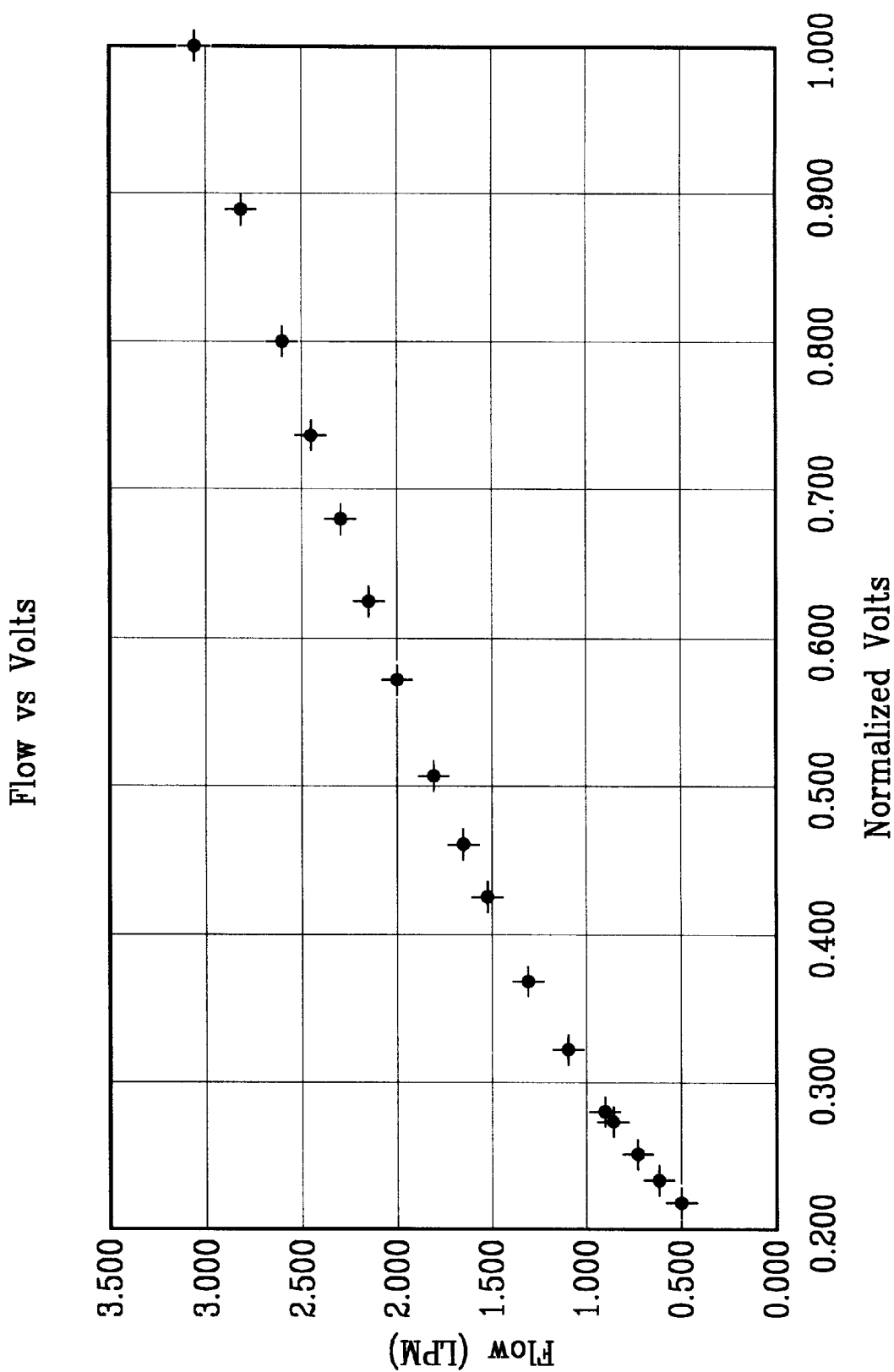
FIG. 2 is a plot of data points collected through a series of tests on a personal air sampler conducted according to our invention.

An example of measurements over a full range is seen in FIG. 2, which is a plot of averages computed of four readings at each of 26 incrementally increased flow settings in liters per minute. The X axis is in terms of volts applied to the pump, in this case to measure the flow resulting at the voltage shown. It will be seen that the plot is not linear. Our invention contemplates calculating a curve from such data so that all possible settings on the sampler can be handled by the feedback loop. At least three data points are needed for such a calculation, and they are preferably obtained by four iterations of the calibration procedure described above at each set point. Any of numerous "best-fit" algorithms may be used. To achieve the optimum balance of accuracy and speed, we use from six to eighteen desired flow set points for curve calculation, most preferably about ten to about fourteen.

While we speak above of using the feedback signal to adjust the voltage of the pump, it may adjust any operating factor which will in turn adjust the pump's output in the desired manner, such as power, a clutch, or the length of stroke. Any type of adjustment which will respond to the feedback signal may be used; the adjustment need not be electrical, nor does the feedback necessarily need to be electrical—it may be pneumatic, for example.

What is claimed is:

1. Method of testing the air processing of a personal air sampler including an electrically driven pump and a means for setting a desired air flow therefrom to said air sampler, comprising (a) setting a desired air flow in said air sampler, (b) generating a signal representing a reading of air flow through said air sampler set at said desired air flow rate, (c) recording said reading in a data recorder (d) repeating steps (b) and (c) through at least one iteration, (e) calculating an average of at least two of said recordings, and (f) comparing said average to said desired flow.

2. Method of claim 1 which is repeated for a plurality of selected air flows.

3. Method of claim 1 wherein if said average deviates from said desired flow rate by more than a predetermined difference, then (g) generating a signal as a function of said deviation for adjusting the voltage to said pump to reduce said deviation to less than said predetermined difference, whereby said sampler is calibrated at said desired air flow.

4. Method of claim 3 wherein said adjusting of said voltage is accomplished by said signal by recording a record value representing voltage necessary for said pump to reduce said deviation to less than said predetermined difference, whereby said record value is used to control said pump whenever said pump is set at said desired air flow rate.

5. Method of claim 3 which is repeated for a plurality of selected air flow rates in said air sampler.

6. Method of claim 3 followed by calculation of a curve representing adjustment of said pump at any selected air flow setting within a range, recording said curve, and employing said curve to control said pump at any desired air flow setting within said range.

7. Method of claim 6 wherein said pump is controlled by adjusting the voltage supplied to said pump.

8. Method of claim 7 wherein said flows are measured at time intervals of 1–60 seconds.

9. Apparatus for calibrating an air sampler comprising (a) an air sampler including a pump (b) a calibrator including a flow transducer, said calibrator connected to said air sampler to measure air flow therein, said transducer including means for generating a signal as a function of air flow in said calibrator, and (c) a controller connected to and interfacing with both said air sampler and said calibrator, said controller including means for (i) initiating a plurality of flow measurements by said transducer at a desired flow rate (ii) means for measuring the flow rates in said flows, averaging said flow measurements and comparing the average to the desired flow, means for relating to said average the total of the differences of said flows from said average, means for generating a control signal as a function of the difference found in said comparison, and means for receiving said control signal and adjusting pump action as a function thereof.

10. Apparatus of claim 9 including means for adjusting pump action as a function of a plurality of averages found at a plurality of air flows.

11. Apparatus of claim 9 including means for recognizing and rejecting spurious flow readings.

12. Method of calibrating a personal air sampler having a variable electrically driven air flow pump comprising (a) providing an electrical input to said pump for powering said pump (b) measuring the air flow generated by said pump while utilizing said electrical input, (c) thereafter providing at least two additional electrical inputs to said pump for powering said pump and measuring the air flow generated by said pump while utilizing said electrical inputs, (d) calculating a curve correlating said electrical inputs to air flows generated by said pump, and (e) adjusting said means for selecting a desired air flow according to said curve.

13. Method of claim 12 wherein step (c) said additional electrical inputs are incrementally different from each other.

14. Method of claim 12 wherein five to seventeen additional electrical inputs are provided in step (c).

15. Method of claim 14 wherein nine to thirteen additional electrical inputs are provided in step (c).

16. Method of claim 12 wherein step (d) is performed by generating a "best-fit" curve.

* * * * *